US010258760B1

(12) United States Patent
Sherpa et al.

(10) Patent No.: US 10,258,760 B1
(45) Date of Patent: *Apr. 16, 2019

(54) COMPUTER SYSTEM FOR DETERMINING A STATE OF MIND AND PROVIDING A SENSORY-TYPE ANTIDOTE TO A SUBJECT

(71) Applicant: AlayaTec, Inc., Palo Alto, CA (US)

(72) Inventors: Trungram Gyaltrul R. Sherpa, Cambridge, MA (US); David H. C. Chen, Palo Alto, CA (US)

(73) Assignee: AlayaTec, Inc., Palo Alto, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 15/390,413

(22) Filed: Dec. 23, 2016

Related U.S. Application Data

(63) Continuation of application No. 15/003,732, filed on Jan. 21, 2016, now Pat. No. 9,566,411.

(51) Int. Cl.
*A61B 5/00* (2006.01)
*A61B 5/0482* (2006.01)
(Continued)

(52) U.S. Cl.
CPC ............ *A61M 21/00* (2013.01); *G16H 40/63* (2018.01); *A61M 2021/0022* (2013.01);
(Continued)

(58) Field of Classification Search
CPC ..... A61B 5/165; A61B 5/02055; A61B 5/486; A61B 5/1118; A61B 5/7282; A61B 5/4809; A61B 5/08; A61B 5/7275; A61B 5/0476; A61B 5/4866; A61B 5/020405; A61B 5/0402; A61B 5/0205; A61B 5/11; A61B 5/7405; A61B 5/7455; A61B 5/7475; A61B 5/053; A61B 5/6802; A61B 5/4806; A61B 5/4815; A61B 5/0482; A61B 5/0478; A61B 5/04845; G09B 19/00; G06F 19/3481;
(Continued)

(56) References Cited

U.S. PATENT DOCUMENTS

| 5,941,906 A | 8/1999 | Barreras |
| 6,488,617 B1 | 12/2002 | Katz |

(Continued)

*Primary Examiner* — Christine H Matthews
*Assistant Examiner* — Joshua Daryl D Lannu
(74) *Attorney, Agent, or Firm* — Schwegman Lundberg & Woessner, P.A.

(57) ABSTRACT

Computer implemented method and system for achieving a preferred state of mind of a user are disclosed. In a first aspect, the method comprises detecting a biological marker (biomarker) of a user utilizing one or more sensors; and inferring a state of mind of the user based upon data received from the one or more sensors that are provided to computational hardware. Finally the method includes providing an antidote to the user if the inferred state of mind is different than the preferred state of mind utilizing an actuator. In a second aspect, the system comprises one or more sensors for detecting a biological marker (biomarker) of the user and computational hardware for inferring a state of mind of the user based upon data received from the one or more sensors. Finally the system includes an actuator for providing an antidote to the user if the inferred state of mind is different than a preferred state of mind.

1 Claim, 8 Drawing Sheets

(51) Int. Cl.
*A61M 21/00* (2006.01)
*A61M 21/02* (2006.01)
*G16H 40/63* (2018.01)

(52) U.S. Cl.
CPC .............. *A61M 2021/0027* (2013.01); *A61M 2021/0044* (2013.01); *A61M 2205/3303* (2013.01); *A61M 2205/50* (2013.01); *A61M 2230/06* (2013.01); *A61M 2230/42* (2013.01); *A61M 2230/50* (2013.01); *A61M 2230/63* (2013.01); *A61M 2230/65* (2013.01)

(58) Field of Classification Search
CPC ................ G06F 21/32; G06F 19/3456; G06F 2203/011; A61N 1/36014; A61N 1/0476; A61N 1/36025; A61N 1/0484; A61N 1/36139; A61N 2/006; A61N 2/02; A61N 1/04; A61N 2/06
See application file for complete search history.

(56) References Cited

U.S. PATENT DOCUMENTS

| | | |
|---|---|---|
| 6,702,767 B1 | 3/2004 | Douglas |
| 2004/0138578 A1 | 7/2004 | Pineda |
| 2015/0351655 A1* | 12/2015 | Coleman .............. A61B 5/0482 600/301 |

\* cited by examiner

US 10,258,760 B1

COMPUTER SYSTEM FOR DETERMINING A STATE OF MIND AND PROVIDING A SENSORY-TYPE ANTIDOTE TO A SUBJECT

RELATED APPLICATION DATA

This application claims the benefit as a continuation of U.S. application Ser. No. 15/003,732, entitled "COMPUTER SYSTEM FOR DETERMINING A STATE OF MIND AND PROVIDING A SENSORY-TYPE ANTIDOTE TO A SUBJECT" and filed on Jan. 21, 2016, the contents of which is hereby incorporated in its entirety.

FIELD OF THE INVENTION

The present invention relates generally to the wellbeing of an individual and more particularly to a system and method for setting an individual's mind to a preferred state.

BACKGROUND

When a person is more focused, or able to be in the person's preferred state of mind, the person can be more productive for whatever he or she is doing. And as the person is productive, he or she can be happier as well. Additionally, when a person needs to rest, the person should have enough good-quality sleep. After the person is well rested, he or she can be healthier. What is desired is a system and method to help a person to set the person's mind in a preferred state, which may be focused, asleep, or other state. The present invention addresses such a need.

SUMMARY

Computer implemented method and system for achieving a preferred state of mind of a user are disclosed. In a first aspect, the method comprises detecting a biological marker (biomarker) of a user utilizing one or more sensors; and inferring a state of mind of the user based upon data received from the one or more sensors that are provided to computational hardware. Finally the method includes providing an antidote to the user if the inferred state of mind is different than the preferred state of mind utilizing an actuator.

In a second aspect, the system comprises one or more sensors for detecting a biological marker (biomarker) of the user and computational hardware for inferring a state of mind of the user based upon data received from the one or more sensors. Finally the system includes an actuator for providing an antidote to the user if the inferred state of mind is different than a preferred state of mind.

DETAILED DESCRIPTION

Figure 1A:
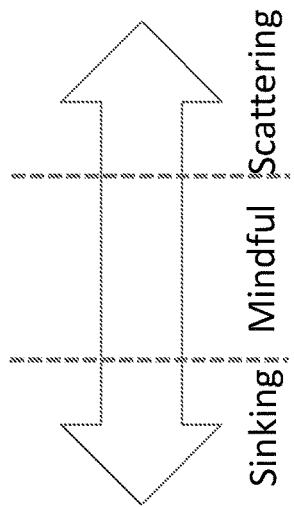
FIG. 1A represents a general categorization of mind states.

The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

Under working conditions, people want to be productive and effective. But, most of the time, they cannot because their minds are untrained and they cannot control their thoughts or emotions. They are easily distracted by unintended thoughts, and the unintended thoughts tend to be followed by agitated emotions. Besides mental distractions of uncontrolled thoughts or emotions, dullness, unclearness, drowsiness and sleepiness are additional situations preventing people from being productive and effective.

Under resting conditions, people may want to sleep. But, many people have difficulties falling into sleep since their minds are too agitated or scattering. They cannot put their minds to rest, and consequently their body cannot rest properly. This condition, especially if prolonged, can cause harms to health.

SCATTERING is a first state of mind, while SINKING is a second state of mind. In between these 2 furthest states, a third state of mind can be categorized as calm, focused, unbiased, awakened, clear, fresh, aware and peaceful. This present technology names the third state of mind as MINDFUL. From time to time, people actually pass the third state of mind though very quickly and without noticing. This present technology may help them to practice balancing their minds, in order to stay in MINDFUL state longer thus their ability to focus is strengthened, for productivity, effectiveness, and most importantly peace and harmony. Alternately, this present technology may help to set a person's mind in sleep, an extreme condition of SINKING. This present technology is for settling a person's mind a state preferred by the person. The preferred state can be MINDFUL, SINKING, or another state.

The SCATTERING state may be further divided into sub-states. Anxiety, pain, surprise, fear, anger, joy, and sadness are some non-limiting examples of the sub-states.

This present technology utilizes at least one sensor to notice, detect, measure, or monitor a person's heart rate (heartbeats), heart rate variability (HRV), blood volume pulse (BVP), respiratory rate (breath), brainwaves (thoughts), blood pressure, body temperature, skin moisture, eye motion, speech pattern, facial expression, hand gesture, body posture, or a combination thereof. This present technology infers a state of mind from the detected physiological or biochemical responses or activities. This present technology may utilize artificial intelligence (AI), neural network, convolutional neural network (CNN), deep learning, or other machine learning algorithm, to conduct the inferring.

When being utilized to train a person's mind to be MINDFUL, this present technology remains silent, quiet, and delivering no antidote when a person stays in MINDFUL. This present technology provides an antidote immediately after the person is leaning toward either of the 2 furthest states (SCATTERING and SINKING), after the person falls into either of the 2 furthest states, when the person stays in either of the 2 furthest states for at least a respective predetermined leeway period, or a combination thereof. By providing an antidote, this present technology helps the person reverse his or her movement toward or deeper into either of the 2 furthest states, and move toward and hopefully stay in MINDFUL. An antidote to SCATTERING state could be similar to or different from an antidote to SINKING state. An embodiment can either model a mind as a continuous spectrum containing 3 general and adjacent states: SINKING, MINDFUL and SCATTERING, or farther divide SCATTERING state into anxiety, pain, surprise, fear, anger, joy, sadness, other sub-state of emotion, or a combination thereof. When an embodiment divides SCATTERING into sub-states, the embodiment may offer different antidote for different sub-states.

When being utilized as a sleeping aid, this present technology remains silent, quiet and delivering no antidote when a person stay in SINKING. This present technology provides an antidote immediately after the person is leaning toward SCATTERING, after the person falls into SCATTERING, when the person stays in SCATTERING for at least a predetermined leeway period of SCATTERING, or a combination thereof. By providing an antidote, this present technology helps the person reverse his or her movement toward or deeper into SCATTERING, and move toward SINKING. When being utilized as a sleep aid, an antidote to SCATTERING could be similar to or different from a SCATTERING antidote when being utilized for training a person to be MINDFUL.

An antidote can be a sound, voice, visible object, vibration, environmental change, or a combination thereof. When the antidote is a voice, it can be a teaching, guidance, instruction, reminder, suggestion, advice, or a combination thereof. The antidote may be actionable to a person. This present technology may present a vocal antidote in different languages. This present technology may allow a person to preselect an antidote from various options.

This present technology may adjust an antidote to avoid over-application, under-application, or both. For example, if a person's mind is not too scattering, the present technology may apply a weaker antidote potentially with an instruction spoken slowly. The present technology may record a history to keep track of how a person responds to a particular antidote. The present technology may adjust strength of an antidote at least partially based on a history. For example, if the person was irresponsive to an antidote and continued to stay in an existing state, this present technology can decide to apply a stronger antidote potentially with an instruction spoken in a stronger tone. This present technology may learn from a history of a current session, an accumulated history of prior sessions, or both. This present technology may present an instruction or teaching in various ways. For example, an instruction or teaching may be presented in different tones, cadence, speed, strength, repetition gap, or a combination thereof.

This present technology may categorize persons (or users) into 2 or more levels. This present technology may be more forgiving to level-1 persons (new users, or beginners) and provide them more allowance, by reducing a sensitivity of a sensor, increasing a predetermined leeway period of SINKING, increasing a predetermined leeway period of SCATTERING, or a combination thereof. By doing so, this present technology allows a wider range of MINDFUL, and narrows a range of SCATTERING, a range of SINKING, or both. This present technology may be less forgiving to level-2 or higher persons, by increasing a sensor sensitivity, reducing either of the two predetermined leeway periods, or a combination thereof. By doing so, level-2 or higher level persons will have a narrower range of MINDFUL. With practice, on each level, a person will progress, require less guidance, and get better. This present technology may automatically promote, recommend, motivate, or otherwise encourage a person to a higher level, when the person is able to remain in a preferred state of mind for a predetermined period of time, a predetermined ratio of time, needing less guidance, or a combination thereof.

This present technology may utilize an application or other kind of software. The application may record a duration of a session, a time log comprising a starting time when a person enters a particular state of mind and a name of the state (e.g. SCATTERING, MINDFUL, or SINKING), a log of any occurrence of an antidote, a chart or other graphical representation of mind's movement in the 3 states, or a combination thereof. When being utilized to train a person's mind to be MINDFUL, the application may motivate a person to continue to use this technology to help the person remain in MINDFUL, by rating his or her record and presenting the rating in an entertaining way. The application should present a higher rating when a person stayed longer in MINDFUL, had a higher ratio of time in MINDFUL, completed a longer or entire session, required or triggered less antidote, or a combination thereof. The application may provide a comparison between the rating and an average or median rating of all persons.

The application may facilitate a self-report by a person. The application may upload or otherwise transfer a self-report, a record, other datum, or a combination thereof. This present technology may utilize a self-report, record, other datum, or a combination thereof to train or test an artificial intelligence (AI), neural network, convolutional neural network (CNN), deep learning, or other machine learning algorithm, for optimizing inferring accuracy, optimizing an antidote, or both.

Visual objects, sound, smell, taste, touch, or mental objects can trigger uncontrolled or unintended thoughts. For example, a person hears a sound of a car. A first thought is the hearing itself, which is directly connected with the person's functional hearing receptor—the ear. A first thought is not the problem. But the person will likely continue immediately from the first thought to additional thoughts often not directly connected to the hearing sensory: e.g. "a red car? . . . "; "my car needs some services tomorrow . . . "; "but I can't bring it to a dealer tomorrow because . . . ". An uncontrolled continuation of unintended thoughts is harmful to our productivity and peace.

Emotions include but not limited to anger, frustration, jealousy, arrogance, greed, depression, excitement, remorse, sadness, empathy, love, and appreciative joy. For example, people could say something very provoking to a person, and stir up the person's emotion. The person will usually follow his or her emotion, and become one who is being directed by the people.

FIG. 1A depicts a general and simple categorization that understands or models a mind as a continuous spectrum containing 3 adjacent states. From the left to the right, there are 3 mental states or states of mind, namely SINKING, MINDFUL, and SCATTERING. SINKING and SCATTERING are 2 furthest states, while MINDFUL is a neutral state, "pure mind" free from either of the furthest states. In SINKING state, one of the 2 furthest states, a person is dull, with unclear mind, drowsy, sleepy or asleep. In SCATTERING state, the other one of the 2 furthest states, a person is distracted with uncontrolled thoughts, controlled by emotions, or both. In between the 2 furthest states, MINDFUL state is neutral and free from SINKING and SCATTERING. In MINDFUL state, a balanced state, a person is calm, focused, unbiased, awakened, clear, fresh, aware and peaceful.

An embodiment may either deploy this simple categorization of 3 general and adjacent states of mind, or additionally split the SCATTERING state into sub-states that comprise anxiety, surprise, fear, anger, joy, sadness, other emotion, or a combination thereof. When an embodiment additionally splits the SCATTERING state into sub-states of mind, the embodiment may apply a different antidote for a different sub-state.

Figure 1B:
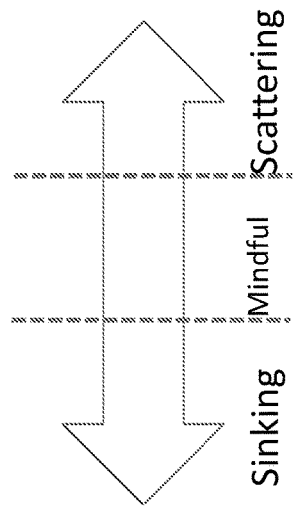
FIG. 1B represents a forgiving categorization of mind states.

FIG. 1B depicts a forgiving division of the 3 states of mind, giving more allowance and a wider range of MINDFUL. This present technology may reduce sensitivity of a sensor with analog or digital means, increase a predetermined leeway period of SINKING, increase a predetermined leeway period of SCATTERING, or a combination thereof, to widen a range within which MINDFUL is defined for a person. By doing so, this present technology will not discourage the person with too many antidotes when the person tries to train his or her mind. This forgiving approach may help a beginner or new user. This disclosure names a beginner or new user as a level-1 person.

Figure 1C:
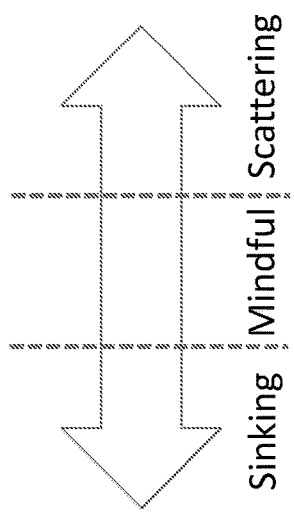
FIG. 1C represents a less forgiving categorization of mind states.

FIG. 1C depicts a less forgiving division of the 3 mental states, giving less allowance and a narrower range of MINDFUL. This present technology may increase sensitivity of a sensor with analog or digital means, reduce a predetermined leeway period of SINKING, reduce a predetermined leeway period of SCATTERING, or a combination thereof, to narrow a range within which MINDFUL is defined for a person. By doing so, this present technology will help a person farther train his or her mind with an early antidote and prevent the person from going too far into a furthest state. This less forgiving approach may help an experienced user. This disclosure names an experienced user as level-2 person. This technology may classify persons or users into 2 or more levels.

Figure 1D:
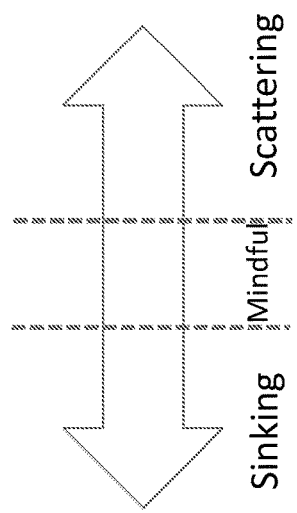
FIG. 1D represents an asymmetrical categorization of mind states.

FIG. 1D depicts an asymmetrical division of the 3 mental states, allowing a boundary between SINKING and MINDFUL and a boundary between MINDFUL and SCATTERING to be defined separately. This present technology allows monitoring a same physiological or biochemical response or activity for inferring all states of mind, or monitoring a different physiological or biochemical response or activity for inferring a different state of mind, or both. A sensor sensibility, a predetermined leeway period, or both can be same or different when inferring a different state of mind.

Though FIG. 1D shows a wider range of Sinking as a non-limiting example, this present technology also allows widening of Mindful state, widening of Scattering state, or any kind of asymmetrical division.

This disclosure defines a biological marker (biomarker) as a measurable broad category of phenomenon, sign, characteristic, activity, event, or feature; indicating a biological process, a body condition, a physiological state, a biochemical response, or a combination thereof. Non-limiting examples of biological marker (biomarker) comprise heart rate or heartbeats, heart rate variability (HRV), blood volume pulse (BVP) or blood flow, respiratory rate or breath, brainwave, skin temperature, skin conductivity, eye motion, speech rate, facial expression, and body posture.

Figure 2A:
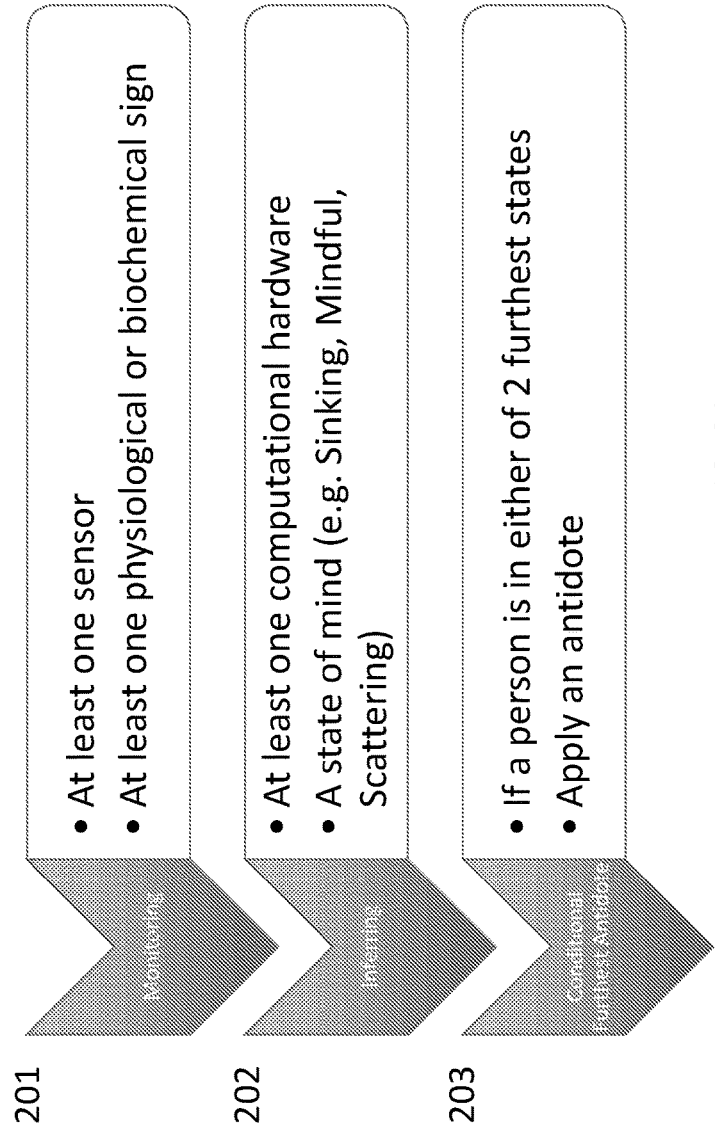
FIG. 2A represents an exemplified and non-limiting process comprising monitoring, inferring, and optional applying antidote, when this present technology is utilized for mind tuning.

FIG. 2A depicts an exemplified and non-limiting process when this present technology is utilized for mind tuning. With Monitoring 201, this present technology utilizes at least one sensor to monitor at least one biological marker (biomarker). With Inferring 202, this present technology infers a state of mind. With Conditional Furthest Antidote 203, this present technology applies an antidote if a person is in either of the 2 furthest states for at least a predetermined leeway period (e.g. 0 to a few seconds); otherwise remains silent, quiet and delivering no antidote. When a predetermined leeway period is 0, an embodiment may apply an antidote immediately.

An embodiment may either conduct a sketchy inferring wherein a state of mind can be SINKING, MINDFUL or SCATTERING; or conduct a detailed inferring wherein the SCATTERING state is sub-divided into anxiety, pain, surprise, fear, anger, joy, sadness, other sub-state of emotion, or a combination thereof. When an embodiment conducts detailed inferring, subsequently the embodiment may apply a different antidote according to which sub-state a person is in.

Figure 2B:
FIG. 2B represents an exemplified and non-limiting process comprising a first set of additional recording, and adjusting, when this present technology is utilized for mind tuning.

FIG. 2B depicts a first extended and non-limiting process when this technology is utilized for mind tuning. In addition to elements 201, 202 and 203, elements 214 and 215 are added. With Antidote Recording 214, this present technology records any antidote applied. Adjusting 215 adjusts an antidote based on a record, a currently inferred state of mind, or both. For example, Antidote Recording 214 may record that an antidote for SCATTERING is applied. Adjusting 215 may find a currently inferred state of mind becomes SINKING soon after being in SCATTERING. In this case, a person becomes SINKING quickly after a SCATTERING antidote was applied. Based on both the record and the current state of mind, this technology may make the antidote for SCATTERING weaker. This is to prevent over-application again, when the person falls into SCATTERING again.

Figure 2C:
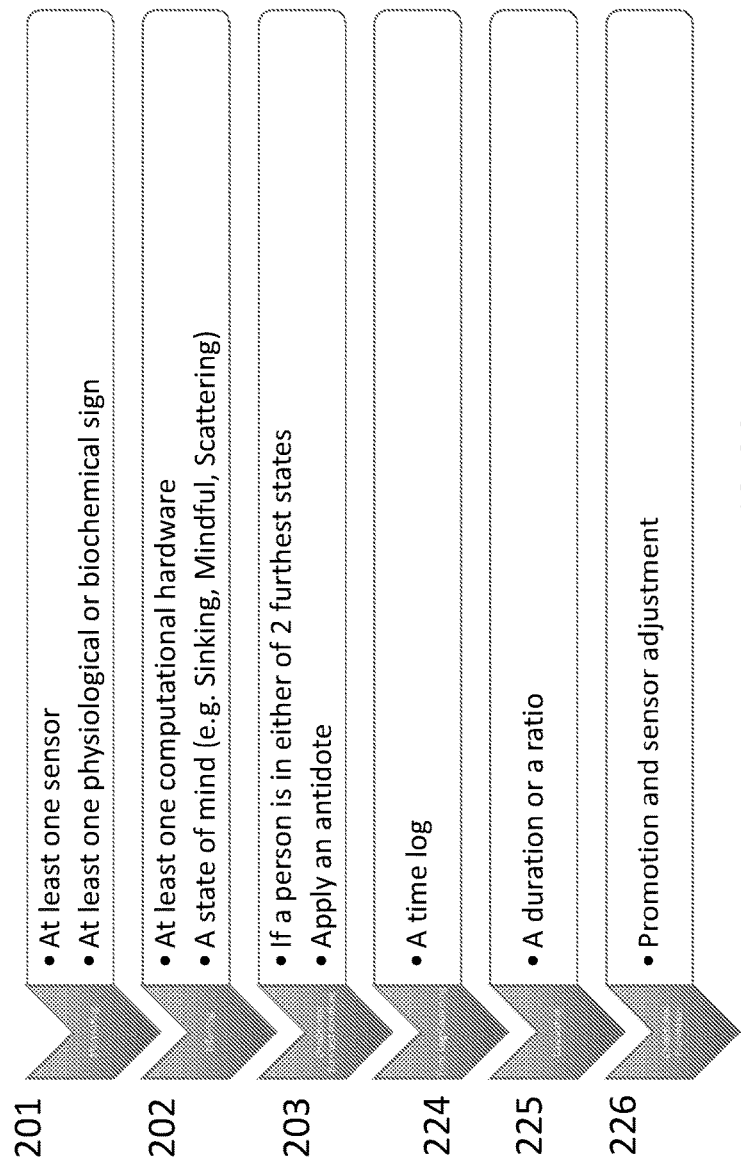
FIG. 2C represents an exemplified and non-limiting process comprising a second set of additional recording, calculating, as well as optional promoting and adjusting, when this present technology is utilized for mind tuning.

FIG. 2C depicts a second extended and non-limiting process when this present technology is utilized for mind tuning. In addition to elements 201, 202 and 203, elements 224, 225, and 226 are added. Time Log Recording 224 records a time log comprising a starting time when a person enters a particular state of mind and a name of the state (e.g. SINKING, MINDFUL, or SCATTERING). Calculating 225 calculates a duration within which a person stays in MINDFUL, a ratio representing a relationship between a total time in MINDFUL and a total time in a session, or both. Conditional Promotion 226 automatically promotes or proactively motivates a person to a higher level of mind tuning, and adjusts sensitivity of the at least one sensor, the predetermined leeway period of SINKING, the predetermined leeway period of SCATTERING, or a combination thereof, if the person is automatically promoted to or actively accepted the higher level of mind tuning.

Figure 3A:
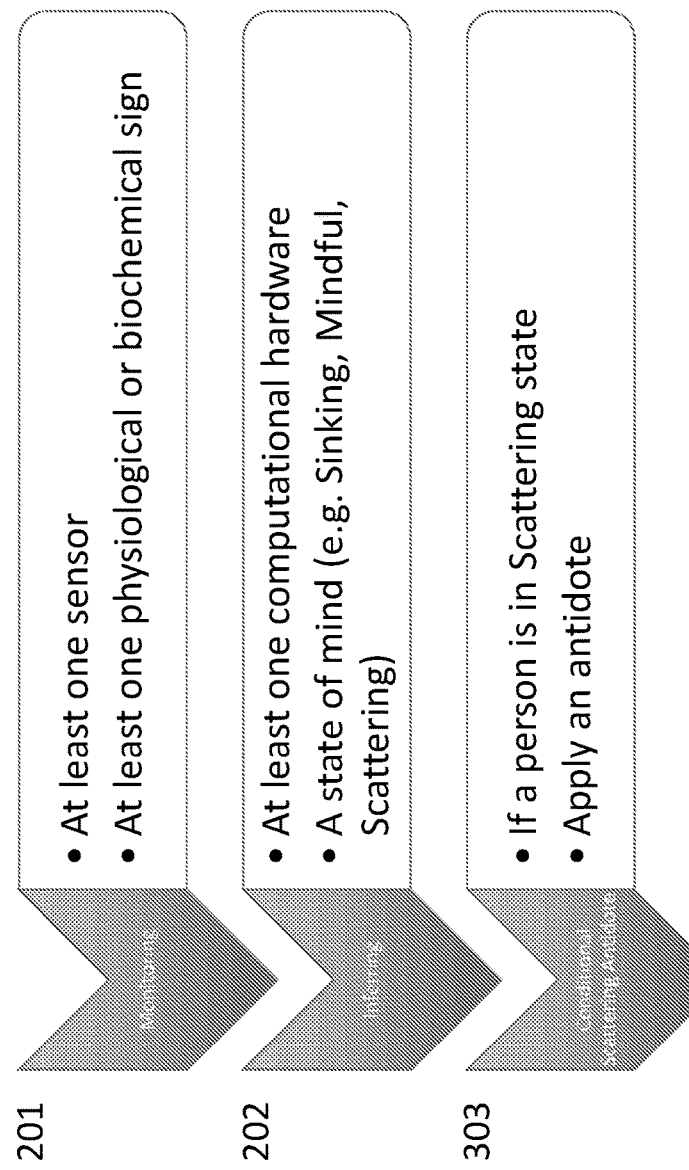
FIG. 3A represents an exemplified and non-limiting process comprising monitoring, inferring, and optional applying antidote, when this present technology is utilized as a sleep aid.

FIG. 3A depicts an exemplified and non-limiting process when this present technology is utilized as a sleeping aid. With Monitoring 201, this present technology utilizes at least one sensor to monitor at least one physiological or biochemical response or activity. With Inferring 202, this present technology infers a state of mind. Conditional SCATTERING Antidote 303 applies an antidote if a person is in SCATTERING state for at least a predetermined leeway period (e.g. 0 to a few seconds); otherwise remains silent, quiet and delivering no antidote. When a predetermined leeway period is 0, an embodiment may apply an antidote immediately.

Figure 3B:
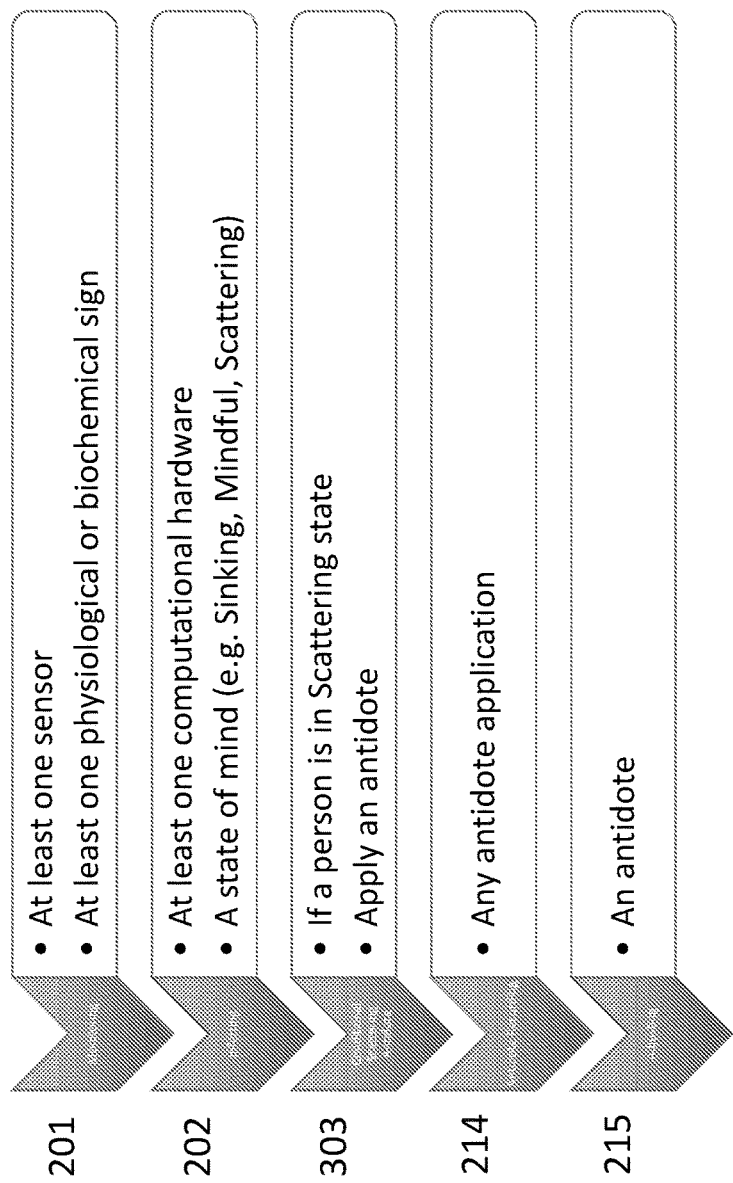
FIG. 3B represents an exemplified and non-limiting process comprising a first set of additional recording, and adjusting, when this present technology is utilized as a sleep aid.

FIG. 3B depicts a first extended and non-limiting process when this technology is utilized as a sleeping aid. In addition to elements 201, 202 and 303, elements 214 and 215 are added. With Antidote Recording 214, this present technology records any antidote applied. Adjusting 215 adjusts an antidote based on a record, a currently inferred state of mind, or both. For example, Antidote Recording 214 may record that an antidote for SCATTERING is applied. Adjusting 215 may find a currently inferred state of mind remains as SCATTERING. In this case, a person remains SCATTERING after a SCATTERING antidote was applied. Based on both the record and the current state of mind, this technology may make the antidote for SCATTERING stronger, select a different SCATTERING antidote, or both. This is to prevent under-application again, and to help a person fall into sleep earlier.

This present technology helps a person to achieve or maintain a preferred state of mind. The preferred state of mind can be MINDFUL or SINKING, as exemplified with above non-limiting descriptions and drawings. Likewise, the preferred state of mind can be SCATTERING as well. When the present technology is embodied to help achieve or maintain the SCATTERING state of mind, the SINKING state and the MINDFUL state are not preferred, but the SCATTERING state is preferred. An embodiment for the SCATTERING state of mind may apply antidote when a person is in SINKING, MINDFUL, or both. An embodiment for the SCATTERING state of mind may utilize a SINKING antidote, which is similar to or different from a SINKING antidote from an embodiment for the MINDFUL state.

Figure 4A:
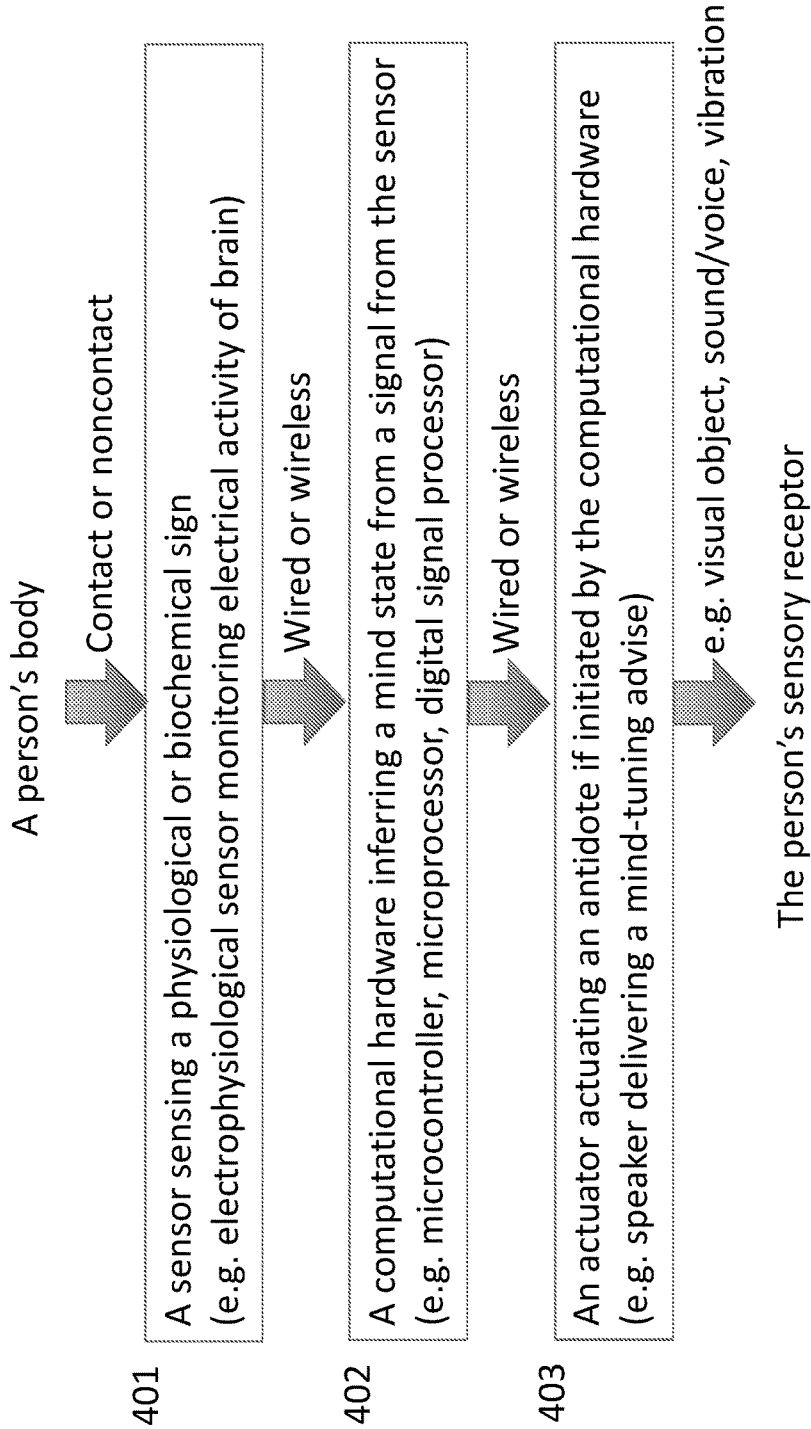
FIG. 4A represents an exemplified and non-limiting embodiment with 3 devices.

FIG. 4A depicts an exemplified and non-limiting connectivity of devices. This non-limiting example is suitable for a mind tuning system, a sleeping aid system, or other system. An embodiment may comprise 3 devices. These 3 devices may be integrated, packaged, or otherwise enclosed inside an enclosure, and appear as a single product such like a fitness wristband, earplug, earphone, headband, headset, smart watch, smart phone, smart glasses, smart wearable, or other product. It is also allowed to have these 3 devices as 2 or more separate products that perform this present technology together.

A first device 401 comprises at least one sensor suitable to obtain, notice, detect, measure, or monitor a person's heart rate or heartbeats, heart rate variability (HRV), blood volume pulse (BVP) or blood flow, respiratory rate or breath, brainwaves, skin temperature, skin conductivity, eye motion, speech rate, facial expression, body posture, other physiological or biochemical response or activity, or a combination thereof. For example, a camera may be used as a sensor for monitoring eye motion, avoidance of eye contact, facial expression, body gesture or posture, or a combination thereof. A photoplethysmography (PPG) sensor, comprising a light-emitting diode (LED) and a photo-detector, may be used to monitor a heart rate (beats per minute), interval from an onset of one R wave to an onset of a next one (R-R interval), heart rate variability (HRV), blood volume pulse (BVP), moving average of blood volume pulse peak-to-peak amplitude variation (MBAV), or a combination thereof. An electroencephalography (EEG) or other electrophysiological sensor may be used to monitor electrical activity of a brain or brainwaves. A webcam with independent component analysis on color channels may be used as a sensor to extract the blood volume pulse (BVP), heart rate, respiratory rate, heart rate variability (HRV), or a combination thereof. An infrared thermometer may be used as a sensor to measure skin or body temperature. A galvanic resistance sensor, comprising 2 silver chloride (AgCl) electrodes and a voltage source, may measure skin conductivity, galvanic skin response (GSR), or both. A microphone may be used as a sensor to measure speech pitch variables, speech rate, or both. A gyroscope sensor (gyro sensor), vibrating structure gyroscope, vibratory gyroscope, or accelerometer may be used as a sensor to measure body posture, body gesture, or both. An embodiment may utilize at least one sensor from these non-limiting examples, a different sensor, or a combination thereof.

A second device 402 comprises at least one microcontroller, microprocessor, digital signal processor (DSP), system on a chip (SoC), or other computational hardware suitable to infer a state of mind from at least one signal from the first device. The second device 402 may treat a transient signal as a noise and ignore it. The second device 402 may infer SINKING from nonlinear eye movement, yawning, heart rate reduction, slower or bigger brainwaves, other indicative physiological or biochemical sign, or a combination thereof. The second device 402 may infer SCATTERING from increased or rapid heart rate (heartbeat), heart rate acceleration, inter-beat interval (IBI) variability reduction, blood volume pulse (BVP) amplitude reduction, increased skin temperature, shortness of breath, increased respiration, fast breathing, other indicative physiological or biochemical sign, or a combination thereof. When neither SINKING nor SCATTERING is inferred, MINDFUL is implied. In such way, an embodiment may utilize the second device 402 for simple inferring with 3 possible results: SINKING, MINDFUL or SCATTERING. Alternately, an embodiment may utilize the second device 402 for detailed inferring by farther breaking down SCATTERING into sub-states. For example, for a detailed inferring, the second device 402 may infer anxiety from avoidance of eye contact. The second device 402 may infer pain from decreased amount of blood currently running through the vessels (BVP). The second device 402 may infer surprise from increased skin conductance level (SCL), increased skin conductance response (SCR), increased heart rate, decreased blood volume pulse (BVP), decreased pulse transit time (PTT), or a combination thereof. The second device 402 may infer fear from faster speech, louder speech, higher or wider pitch range, or a combination thereof. The second device 402 may infer sadness from lower-pitched and slurred speech, slower speech, or both.

The second device 402 may classify or infer a state of mind by using a database, knowledge base, vector space model, statistical method, optical flow, active appearance model, linear discriminant classifier (LDC), k-nearest neighbor (k-NN), Gaussian mixture model (GMM), discriminant function analysis (DFA), linear discriminate analysis (LDA), classification and regression tree (CART), self-organizing map (SOM), Naïve Bayes algorithm, support vector machine (SVM), artificial intelligence (AI), artificial neural network (ANN), convolutional neural network (CNN), decision tree algorithm, hidden Markov model (HMM), deep learning, other machine learning algorithm, or a combination thereof. The second device 402 may confirm an inferring immediately, or after a same state is inferred for a predetermined leeway period (e.g. 3 to 10 seconds). The second device 402 may maintain a same predetermined leeway period for both SINKING and SCATTERING, or a different predetermined leeway period for each of the 2 furthest states.

When being utilized for mind tuning, the second device 402 initiates an antidote after confirming a person is in either SINKING or SCATTERING state. The second device 402 may record a state confirmation with a name of the state and a timestamp. After confirming a state of mind, the second device 402 may review a last record to check if the current state is same as a last recorded state. If the current state is same as the last recorded one, the second device 402 may initiate a stronger antidote. Otherwise, the second device 402 may initiate an existing or weaker antidote. The second device 402 may compute a maximum duration during which a person remains in MINDFUL without triggering an antidote, a ratio representing a relationship between a total time in MINDFUL and a total time in a session, a length of longest session completed, or a combination thereof. The second device 402 may automatically promote or proactively motivate a person to a higher level of mind tuning. If the person is automatically promoted or actively consents to the higher level, the second device 402 may increase a sensitivity of a sensor potentially by adjusting a digital filter, decrease the predetermined leeway period of SINKING, decrease the predetermined leeway period of SCATTERING, or a combination thereof.

When being utilized as a sleep aid, the second device 402 initiates an antidote after confirming a person is in either MINDFUL or SCATTERING state. The second device 402 may record a state confirmation with a name of the state and a timestamp. After confirming a state of mind, the second device 402 may review a last record to check if the current state is same as a last recorded state. If the current state is same as the last recorded one, the second device 402 may initiate a stronger antidote. Otherwise, the second device 402 may initiate an existing or weaker antidote. The second device 402 may compute a maximum duration during which a person remains in SINKING (e.g. asleep) without triggering an antidote, a ratio representing a relationship between a total time in SINKING and a total time in a session, a length of longest session completed, or a combination thereof.

The second device 402 may facilitate a self-report by a person, potentially via an application or other kind of software. The second device 402 may utilize a self-report to correlate or otherwise optimize the inferring, an antidote, or both. The second device 402 may upload or otherwise transfer a self-report, a record, other datum, or a combination thereof. This present technology may utilize the uploaded or transferred information to train, test, or otherwise optimize an embodiment, potentially utilizing artificial intelligence (AI), neural network, convolutional neural network (CNN), deep learning, or other machine learning algorithm.

A third device 403 comprises at least one actuator, wired or wirelessly coupled to the second device 402, to actuate an antidote by means of sounds, voices, visible objects, vibration, environmental control, or a combination thereof. For example, a prominent vibrator may be used as an actuator to generate a sound, vibration, or both. A speaker may be used as an actuator to synthesize, play back, or otherwise generate voices. A display may be used as an actuator to present visible objects. A light switch or dimmer may be used as an actuator to control ambient lighting. An embodiment may utilize at least one actuator from these non-limiting examples, a different actuator, or a combination thereof. An embodiment may utilize 2 or more actuators to allow a person to choose from different kinds of antidote.

The third device 403 may record or otherwise store a teaching, guidance, instruction, reminder, suggestion, or a combination thereof, as an antidote. The teaching, guidance, instruction, reminder, or suggestion may have multiple versions, in different languages, to allow choices of languages. The teaching, guidance, instruction, reminder, or suggestion may have various presentations, in terms of tones, cadence, speed, or a combination thereof, as antidotes of different strengths. Non-limiting examples of teaching, guidance, instruction, reminder, or suggestion in English are "settle the mind on the breath", "awareness rests on breath as it enters and leaves the body", and "when thoughts arise, simply let them go".

Figure 4B:
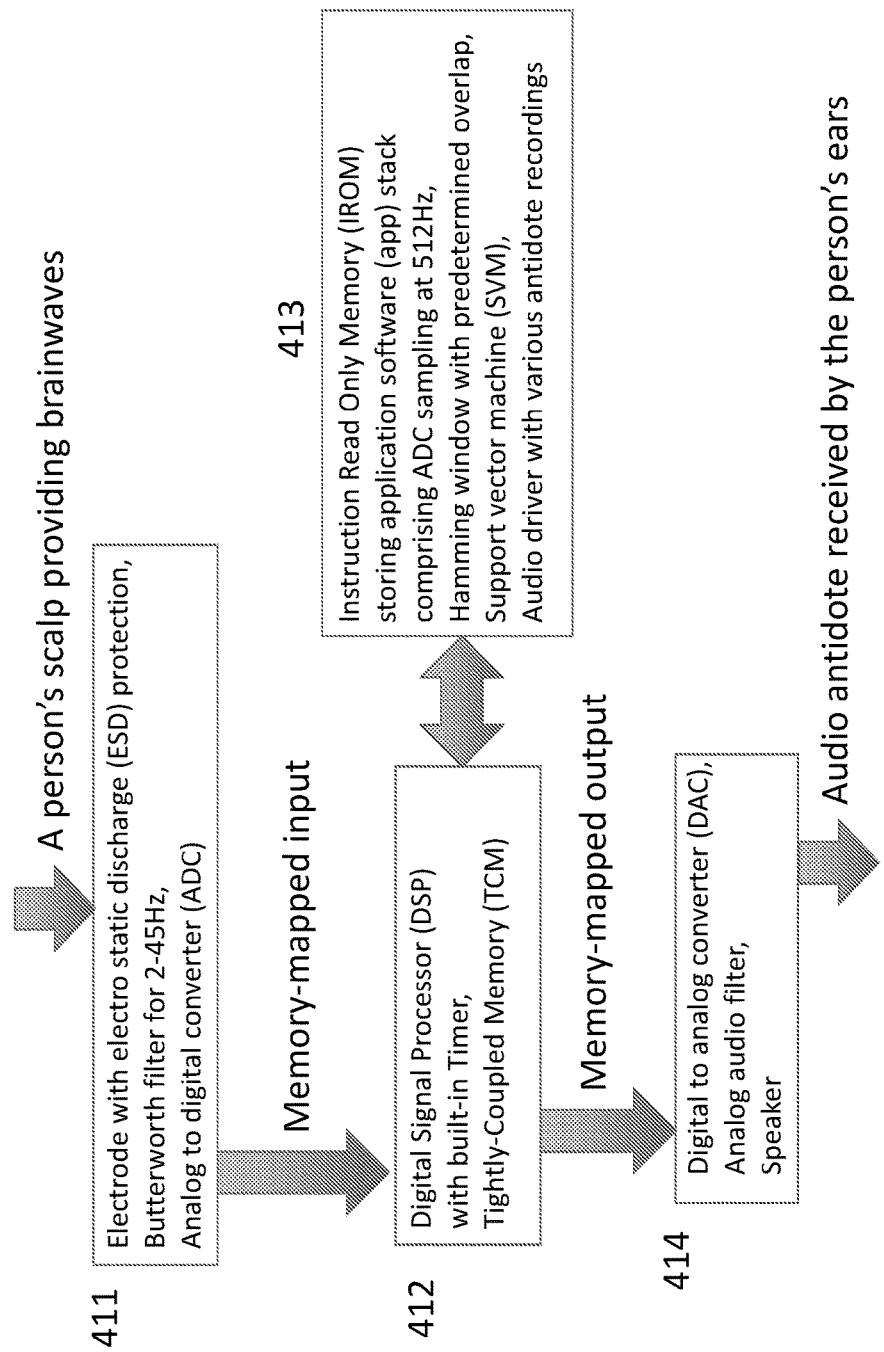
FIG. 4B represents an exemplified and non-limiting embodiment with detailed hardware block diagram.

FIG. 4B depicts a non-limiting embodiment with detailed hardware diagrams wherein a brainwave is selected as a biological marker (biomarker) and voices are selected as a means of antidotes. This non-limiting hardware diagram is suitable for a mind tuning system, a sleeping aid system, or other system. The brainwave is detectable in contact or contactless around a person's scalp. The non-limiting embodiment utilizes an electrode 411, made of silver chloride (AgCl), to receive the brainwave. The electrode transmits the brainwave as a low voltage analog signal, which is filtered with a Butterworth filter configured to pass signals from 2 cycles per second (Hz) to 45 Hz. A filtered 2-45 Hz analog signal is converted into a digital signal, by an analog to digital converter (ADC), such as Texas Instruments ADS1291 or another similar or better low-power analog front-end for bio-potential measurements.

A digital signal processor (DSP) 412 is built with a timer and configured with a tightly coupled memory (TCM). An instruction read only memory (IROM) 413 is coupled with the DSP 412 to provide instructions in form of an application (app) software stack. The application software stack comprises ADC sampling instructions, to instruct the DSP 412 to sample the digital signal from the ADC at a predetermined rate or frequency via a memory-mapped input port. The digital signal is processed in parallel with 2 Hamming windows to obtain a short-time Fourier transform (SIFT) spectrum, to determine frequency contents of the digital signal as it changes over time. The DSP 412 executes a trained support vector machine or multiclass support vector machine (SVM) to analyze the SIFT spectrum, and classifies or infers the spectrum into a state of mind.

The DSP 412 may utilize the TCM for Antidote Recording 214, Time Log Recording 224, Calculating 225, other software tasks, or a combination thereof. The DSP 412 may adjust a coefficient of one of the Hamming windows to vary sensitivity to a corresponding brainwave frequency, which may indicate either SINKING or SCATTERING. The DSP 412 may utilize the timer as an adjustable predetermined leeway period for SINKING, as an adjustable predetermined leeway period for SCATTERING, or both. Varying sensitivity, adjusting a leeway period, or both is a way to realize Adjusting 215, Conditional Promotion 226, or both.

If the DSP 412 classifies or infers a state of mind other than a predetermined preferred state of mind, the DSP 412 initiates an audio driver to play back a prerecorded antidote voice. The antidote voice is transmitted onto a memory-mapped output port. A digital to analog converter (DAC) converts the digital antidote voice into an analog signal, which is then filtered with an analog audio filter. A speaker 413 converts a filtered audio signal into a corresponding voice, perceptible by the person's ears. The person may practice on, apply, or utilize an actionable advice conveyed in the voice.

The non-limiting embodiment, depicted by FIG. 4B, can also be applied to pre-train a SVM, in a supervised learning. The supervised learning provides a set of training examples, each marked for belonging to one of states of mind. With the training examples, the SVM builds a model that later assigns a set of testing examples to states of mind. After the SVM correctly assigns the test examples to their respective states of mind, the SVM is successfully trained.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A computer implemented method for mind tuning to a preferred state of mind of a user, the method comprising:

providing a computer system configured to tune the mind of the user to the preferred state;

converting at least one biomarker of the user to computer readable data by utilizing one or more sensors that sends signals based on the at least one biomarker;

inferring, with computational hardware, a state of mind of the user based upon data received from the one or more sensors;

providing an antidote or countermeasure of sensory-type stimulation for the user responsive to the inferred state of mind being different than the preferred state of mind utilizing an actuator, wherein a mindful or sinking state is predetermined as the preferred state; and providing a second antidote or countermeasure of sensory-type stimulation to the user that is stronger or weaker than the antidote or countermeasure, responsive to the inferred state of mind remaining different from the preferred state of mind after the antidote or countermeasure is provided.

\* \* \* \* \*